United States Patent [19]
Jubin, Jr. et al.

[11] Patent Number: 5,523,426
[45] Date of Patent: *Jun. 4, 1996

[54] INTEGRATED PROCESS FOR EPOXIDATION

[75] Inventors: John C. Jubin, Jr., West Chester, Pa.;
Guy L. Crocco, Wilmington, Del.;
John G. Zajacek, Devon, Pa.

[73] Assignee: ARCO Chemical Technology, L.P., Greenville, Del.

[*] Notice: The term of this patent shall not extend beyond the expiration date of Pat. No. 5,384,418.

[21] Appl. No.: 368,175

[22] Filed: Jan. 4, 1995

[51] Int. Cl.⁶ .................... C07D 301/12; C07D 303/04
[52] U.S. Cl. ............................................................ 549/531
[58] Field of Search ............................................. 549/531

[56] References Cited

U.S. PATENT DOCUMENTS

| | | | |
|---|---|---|---|
| 3,953,362 | 4/1976 | Lines et al. | 252/431 |
| 4,009,122 | 2/1977 | Lines et al. | 252/431 |
| 4,157,734 | 6/1979 | Lines et al. | 260/348.31 |
| 4,824,976 | 4/1989 | Clerici et al. | 549/531 |
| 4,833,260 | 5/1989 | Neri et al. | 539/531 |
| 4,937,216 | 6/1990 | Clerici et al. | 502/62 |
| 5,166,372 | 11/1992 | Crocco et al. | 549/531 |
| 5,214,168 | 5/1993 | Zajacck et al. | 549/531 |
| 5,221,795 | 6/1993 | Clerici et al. | 549/531 |
| 5,252,758 | 10/1993 | Clerici et al. | 549/531 |
| 5,262,550 | 11/1993 | Crocco et al. | 549/531 |
| 5,354,875 | 10/1994 | Nemeth et al. | 549/531 |
| 5,374,747 | 12/1994 | Sakton et al. | 549/531 |
| 5,384,418 | 1/1995 | Zajacek et al. | 549/531 |

FOREIGN PATENT DOCUMENTS 573887 12/1993 European Pat. Off. .
4-59769 2/1992 Japan .
6-211821 8/1994 Japan .

OTHER PUBLICATIONS

"Synthesis of Propylene Oxide from Propylene & Hydrogen Peroxide Catalyzed by Titanium Silicalite" Journal of Catalysis 129 159–167 (1991), Clerici et al.

"Synthesis & Catalytic Properties of Titanium Containing Zeolites", *Innovation in Zeolite Materials Science*, pp. 413–425 (1988).

M. Clerici et al., "Epoxidation of Lower Olefins with Hydrogen Peroxide & Titanium Silicalite" pp. 71–83 (1993).

Huybrechts et al. "Factors Influencing the Catalytic Activity of Titanium Silicalites in Selective Oxidations", pp. 237–244 (1991).

Takashi Tatsumi et al., "Shape Selective Epoxidation of Alkenes Catalysed by Titanosilicate", 1990, pp. 297–298.

Clerici et al., "Synthesis of Propylene Oxide from Propylene & Hydrogen Peroxide Catalyzed by Titanium Silicalite" (1991) pp. 344–346.

*Primary Examiner*—Joseph E. Evans
*Attorney, Agent, or Firm*—Stephen D. Harper

[57] ABSTRACT

Epoxides are produced by an integrated process involving molecular oxygen oxidation of a secondary alcohol, separation of the ketone by-product, and epoxidation of an olefin in the presence of a titanium silicalite catalyst and a diluent, wherein a crude alcohol stream obtained by removing epoxide from the epoxidation product mixture serves as the diluent. Despite use of the crude alcohol stream, which typically comprises water, organic acids and glycols, high selectivities to epoxides such as propylene oxide are realized.

19 Claims, 1 Drawing Sheet

5,523,426

INTEGRATED PROCESS FOR EPOXIDATION

FIELD OF THE INVENTION

This invention relates to an integrated process for producing an epoxide. In particular, the invention pertains to an epoxidation method wherein the crude alcohol stream obtained by removing epoxide from the epoxidation reaction mixture is used to dilute a concentrated oxidant stream used as a source of hydrogen peroxide in the epoxidation step.

BACKGROUND OF INVENTION

Many different methods for the preparation of epoxides have been developed. One such method involves the use of certain titanium silicalite materials to catalyze olefin oxidation by hydrogen peroxide. This method is described, for example, in U.S. Pat. No. 4,833,260, which discloses a procedure (Example 35) wherein propylene is converted to propylene oxide. An isopropanol/water mixture is reacted with oxygen at 135° C. to afford a mixture containing hydrogen peroxide. The mixture is thereafter used directly in a titanium silicalite-catalyzed epoxidation of propylene without intervening treatment or fractionation.

U.S. Pat. No. 5,384,418 (corresponding to application Ser. No. 08/241,215, filed May 10, 1994) describes an integrated process for epoxide production which also employs hydrogen peroxide derived from isopropanol oxidation in a titanium silicalite-catalyzed epoxidation, but teaches that removal of substantially all of the acetone from the isopropanol oxidant prior to use in epoxidation is advantageous. The patent additionally suggests that isopropanol derived from hydrogenation of the removed acetone could be employed to dilute the isopropanol oxidant to achieve the desired $H_2O_2$ concentration within the epoxidation reactor. Under certain conditions, it is desirable to maintain relatively dilute (i.e., 1–10 weight %) maximum hydrogen peroxide concentrations during epoxidation since higher concentrations can result in poorer epoxide selectivity.

We have now unexpectedly discovered that a crude alcohol stream obtained by removing epoxide from the reaction product mixture exiting the epoxidation reactor can also be used for the purpose of diluting the hydrogen peroxide feed to the reactor. This result was surprising, since titanium silicalite-catalyzed epoxidations are known to be sensitive to the presence of trace impurities. U.S. Pat. No. 4,824,976, for example, indicates that the addition of certain basic substances to a titanium silicalite-catalyzed epoxidation mixture helps to minimize acid-catalyzed non-selective ring-opening reactions of the desired epoxide. As the aforementioned crude alcohol stream typically contains, in addition to isopropanol and water, measurable amounts of relatively heavy (high boiling) organic acids, glycols, and so forth, it would have been expected that the use of this crude alcohol stream to dilute the hydrogen peroxide feed to the epoxidation reactor would result in poorer yields of epoxide. Instead, we have now found that little or no loss of selectivity to epoxide takes place when such dilution is practiced as compared to the use of purified or refined isopropanol.

SUMMARY OF THE INVENTION

This invention provides an integrated epoxidation process comprising (a) reacting a $C_3$-$C_4$ secondary alcohol and molecular oxygen in a liquid phase to form an oxidant mixture comprised of the $C_3$-$C_4$ secondary alcohol, a $C_3$-$C_4$ aliphatic ketone corresponding to the $C_3$-$C_4$ secondary alcohol, and hydrogen peroxide;

(b) separating substantially all of the $C_3$-$C_4$ ketone from the oxidant mixture to provide a concentrated hydrogen peroxide-containing stream comprised of $C_3$-$C_4$ secondary alcohol, hydrogen peroxide, and less than 1 weight percent $C_3$-$C_4$ ketone;

(c) reacting the concentrated hydrogen peroxide-containing stream with a $C_2$-$C_4$ olefin in the presence of a titanium silicalite catalyst and a diluent to form an epoxidation reaction mixture comprised of a $C_2$-$C_4$ epoxide corresponding to the $C_2$-$C_4$ olefin, water, and the secondary alcohol;

(d) separating substantially all of the $C_2$-$C_4$ epoxide from the epoxidation reaction mixture to form a crude alcohol stream comprised of the water, $C_3$-$C_4$ secondary alcohol and less than 1 weight percent of the $C_2$-$C_4$ epoxide; and (e) recycling at least a portion of the crude alcohol stream for use as at least a portion of the diluent in step (c).

DETAILED DESCRIPTION OF THE INVENTION

Figure 1:
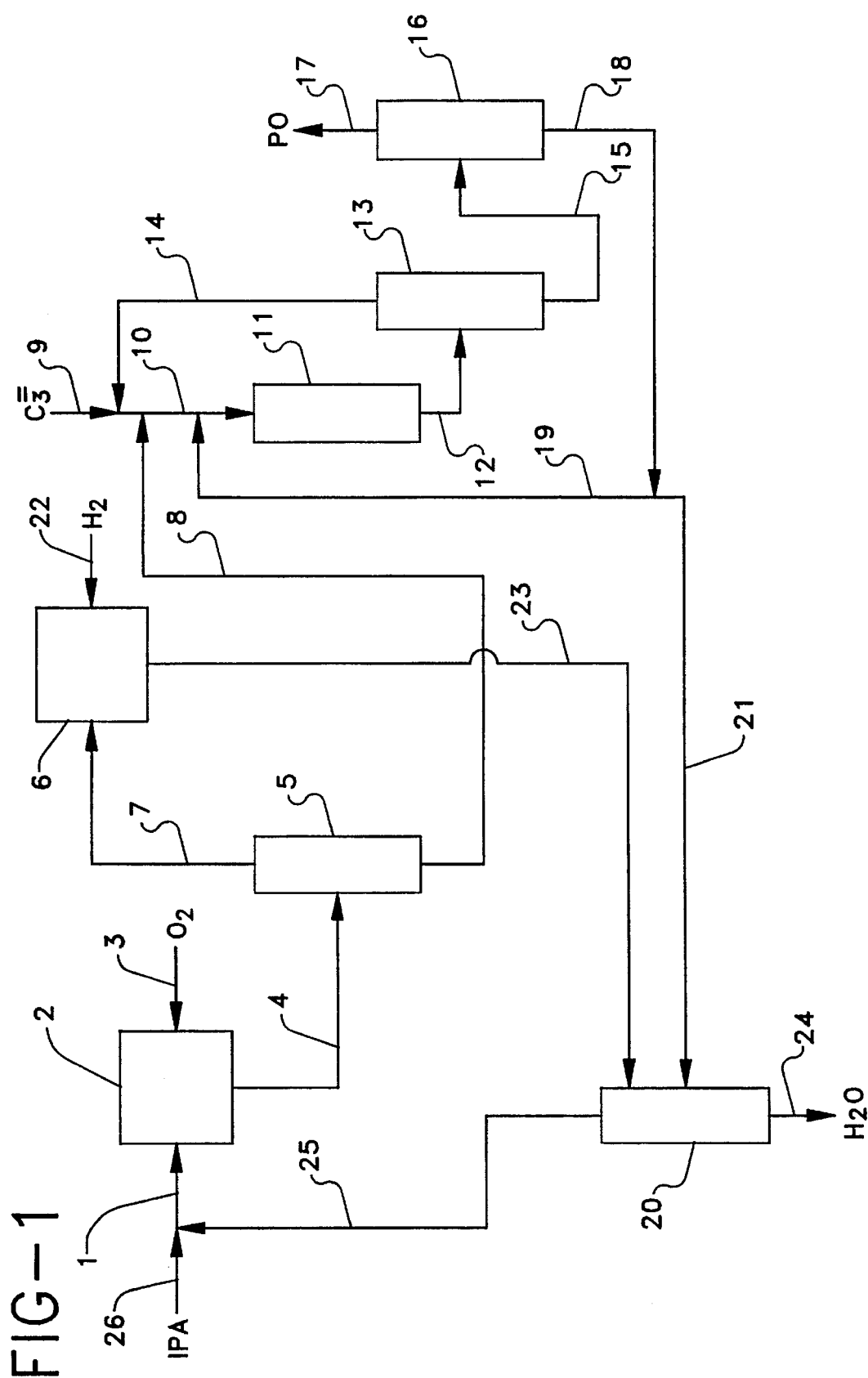
FIG. 1 illustrates in schematic form a suitable embodiment of the process of the invention.

The $C_3$-$C_4$ secondary alcohols suitable for use include isopropanol (isopropyl alcohol) and sec-butanol (sec-butyl alcohol).

The secondary alcohol is reacted with molecular oxygen (dioxygen) from a suitable source such as air to yield an oxidant mixture, which will typically contain excess secondary alcohol, the $C_3$-$C_4$ ketone resulting from oxidation of the secondary alcohol and having the same hydrocarbon skeleton as the alcohol (e.g., acetone or 2-butanone), hydrogen peroxide and water. The starting material to be oxidized may contain minor amounts of the ketone and/or water in addition to the alcohol. For example, the azeotrope of water and isopropanol (87.2 wt % isopropanol, 12.2 wt % water) may be used to advantage. In one embodiment, the oxidizer feed comprises 5 to 20 weight % water, 80 to 95 weight % isopropanol, less than 1 weight % methanol, and less than 3 weight % acetone. Generally speaking, the oxidation conditions are adjusted so as to yield an oxidant mixture comprised of 40 to 90 weight percent secondary alcohol, from about 5 to 25 weight percent hydrogen peroxide, 5 to 35 weight percent of the ketone, and 0 to 35 weight percent water. Partial conversion of the secondary alcohol is accomplished (e.g., from 5 to 50%) such that the unreacted secondary alcohol may be utilized as a carrier or solvent for the hydrogen peroxide and olefin during epoxidation. Residence, hold-up or reaction times of from about 0.25 hours to 4 hours will typically be sufficient for this purpose. The oxidation may be either uncatalyzed or catalyzed (for example, by introduction of a minor amount of a peroxide or hydroperoxide such as t-butyl hydroperoxide). Temperatures of from 50° to 200° C. (more preferably, from 100° to 180° C.) will typically be appropriate for use in order to attain reasonable oxidation rates. The preferred range of oxygen partial pressure in the feed gases (which may include an inert diluent gas such as nitrogen in addition to oxygen) is 1 to 250 psia (more preferably, 5 to 50 psia; most preferably, 10 to 30 psia) partial pressure. Total pressure in the oxidation reaction zone should be sufficient to maintain the components of the reaction mixture in the liquid phase (50 psia to 1000 psia is normally sufficient). A plurality of oxidation reaction zones maintained at different temperatures and pressures may be employed. The alcohol oxidation may be performed in a continuous manner using, for example, a continuous stirred tank reactor (CSTR).

Prior to use in the epoxidation step of this process, the ketone is substantially separated or removed from the oxidant mixture. Any known separation method or technique which is suitable for this purpose may be utilized, including fractionation procedures.

Preferably, however, the oxidant mixture is fractionally distilled whereby the ketone is vaporized and removed from the oxidant mixture as an overhead stream. The concentrated hydrogen peroxide-containing stream obtained by such a procedure thus may comprise a bottoms fraction. Such fractionation may be facilitated by the application of heat and/or reduced (subatmospheric) pressure. Where acetone is to be removed, a pressure of from 5 to 30 psig and a bottoms temperature of from 90° to 125° C. may be utilized, for example. The ketone concentration in the concentrated hydrogen peroxide-containing stream thereby produced should be less than 1 weight percent (more preferably, less than 0.5 weight percent). To minimize the accumulation of any ketone/hydrogen peroxide adducts having peroxy character, this separation is most preferably performed directly after molecular oxygen oxidation. Thus, the oxidant mixture exiting from the oxidizer zone is preferably taken into a distillation column without intervening storage or retention. To accomplish rapid and complete removal of the ketone from the oxidant mixture, it may be desirable to also take overhead some portion of the secondary alcohol and/or water. In one embodiment, for example, the overhead stream may comprise 10 to 80 mole % ketone, 15 to 60 mole % secondary alcohol, and 5 to 30 mole % water. However, for safety reasons, care must be taken not to overly concentrate the hydrogen peroxide in the bottoms fraction nor to have any appreciable amount of hydrogen peroxide in the overhead stream. The residence time in the distillation step is also important. The residence time must be sufficient to accomplish substantial reversal of any ketone/hydrogen peroxide reaction products generated during molecular oxygen oxidation or thereafter to bring the level of aliphatic ketone peroxides to less than 0.5 weight percent total. Excessive residence time should be avoided, however, to avoid excessive decomposition of the hydrogen peroxide. In one preferred embodiment of the invention, a residence time of 10 to 45 minutes (more preferably, 15 to 30 minutes) at 90° to 130° C. (more preferably, 100° to 120° C.) is employed. Under these conditions, it has been found that the desired removal of ketone and conversion of any ketone peroxides present may be readily achieved with minimal loss (<2%) of the hydrogen peroxide in the oxidant mixture. Improved results may be obtained by carefully passivating the distillation column and/or treating the oxidant mixture so as to remove or counteract any species which might catalyze the decomposition of hydrogen peroxide or formation of ketone peroxides. Extractive distillation techniques may also be advantageously used. Other separation procedures capable of reducing the ketone content of the oxidant mixture without significant loss of the hydrogen peroxide contained therein may also be used including, for example, absorption, countercurrent extraction, membrane separation, and the like. Fractionation techniques wherein multiple stages are employed are especially suitable.

As a consequence of the removal of the ketone from the oxidant, the concentration of hydrogen peroxide is increased. The concentrated hydrogen peroxide stream thus will typically contain from 5 to 30 weight percent $H_2O_2$; in one embodiment of the invention, said stream will be comprised of greater than 10 weight percent $H_2O_2$.

In the epoxidation step of the process of this invention, the concentrated hydrogen peroxide-containing stream is contacted with a $C_2$-$C_4$ olefin and a catalytically effective amount of a titanium silicalite at a temperature of from 25° C. to 120° C. (more preferably, 40° C. to 80° C.) to convert the substrate to the desired epoxide. A diluent is also present, wherein a crude alcohol stream recovered after removal of epoxide from the epoxidation reaction mixture is utilized as at least a portion of said diluent. The remainder of the diluent, if any, may be fresh secondary alcohol, secondary alcohol obtained by hydrogenation of the ketone removed from the oxidant mixture, or a different, suitable co-solvent such as methanol. Preferably, the diluent is comprised predominantly (e.g., ≧70%) of the crude alcohol stream. The amount of diluent employed preferably is sufficient to provide a hydrogen peroxide concentration of from 1 to 10 weight percent relative to the total weight of hydrogen peroxide, secondary alcohol, water and additional components of the feed into the epoxidation zone (other than olefin). Sufficient diluent is introduced such that the hydrogen peroxide concentration is reduced at least 10% (more preferably at least 20%) on a relative basis as compared to the $H_2O_2$ level in the undiluted concentrated hydrogen peroxide-containing stream.

Suitable $C_2$-$C_4$ olefins include ethylene, propylene, 1-butene, isobutylene, 2-butene and the like.

The amount of olefin relative to the amount of hydrogen peroxide is not critical, but the molar ratio of olefin: hydrogen peroxide may suitably be from about 100:1 to 1:10. The molar ratio of olefin to hydrogen peroxide is more preferably in the range of from 1:2 to 10:1 (most preferably, 1:1 to 6:1).

In one embodiment of the process of this invention, the feed to the epoxidation reactor (exclusive of the olefin to be epoxidized) comprises 1 to 10 weight percent hydrogen peroxide, 50 to 80 weight percent secondary alcohol, and 10 to 35 weight percent water. Despite the relatively high proportion of water present in such embodiment, epoxide selectivity is surprisingly high with minimal hydrolysis of the epoxide to glycol.

The titanium silicalites useful as catalysts in the epoxidation step of the process comprise the class of zeolitic substances wherein titanium is substituted for a portion of the silicon atoms in the lattice framework of a molecular sieve. Such substances are well-known in the art. Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta. The titanium silicalite preferably contains no non-oxygen atoms other than titanium and silica in the lattice framework, although minor amounts of boron, iron, aluminum, gallium, and the like may be present.

Epoxidation catalysts suitable for use in the process of this invention have a composition corresponding to the following empirical formula $xTiO_2$: $(1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of relatively titanium-rich silicalites may be desirable.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity and the type of reactor or reaction system (i.e., batch vs. continuous) employed. Typically, however, in a batch type epoxidation, the amount of catalyst will be from 0.001 to 10 grams per mole of olefin. In a fixed bed system, the optimum quantity of catalyst will be influenced by the flow rate of reactants through the fixed bed (generally, from about 1 to 100 moles $H_2O_2$ per kilogram of catalyst per hour).

The catalyst may be utilized in powder, pellet, microspheric, extruded, monolithic or any other suitable physical form. The use of a binder (co-gel) or support in combination with the titanium silicalite may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide.

The catalyst may be treated with a basic substance or a silylating agent so as to reduce the surface acidity, as described in U.S. Pat. No. 4,937,216.

The epoxidation reaction temperature is preferably from 25° C. to 120° C. (more preferably, from 40° C. to 80° C.), which in the process of this invention has been found to be sufficient to accomplish selective conversion of the olefin to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase should be utilized. At a reaction temperature of approximately 60° C., for instance, the pressure may advantageously be maintained at approximately 190–220 psig.

The epoxidation step of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations using hydrogen peroxide will generally also be suitable for use. Thus, the reactants may be combined all at once or sequentially. For example, the concentrated hydrogen peroxide-containing stream, the diluent, and/or the olefin may be added incrementally to or at different points within the reaction zone. It will, however, generally be advantageous to control the addition of the various components such that the unreacted hydrogen concentration does not exceed 10 weight % at any point within the reaction zone.

After separating from the epoxidation reaction mixture by any suitable method such as filtration (as when a slurry reactor is utilized, for example), the recovered titanium silicalite catalyst may be economically re-used in subsequent epoxidations. Where the catalyst is deployed in the form of a fixed bed, the epoxidation product withdrawn as a stream from the epoxidation zone will be essentially free of catalyst with the catalyst being retained within the epoxidation zone. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment.

When the olefin and hydrogen peroxide have reacted to the desired level of conversion, the resulting epoxidation reaction mixture comprised of water, $C_2$-$C_4$ epoxide, and $C_3$-$C_4$ secondary alcohol is further treated so as to separate substantially all of the epoxide from the mixture to form a crude alcohol stream comprised of water, the $C_3$-$C_4$ secondary alcohol and less than 1 weight percent of the $C_2$-$C_4$ epoxide. Such separation may most readily be accomplished by distillative means (e.g., fractional distillation) as the secondary alcohol may be selected so as to be substantially higher boiling than the epoxide being produced and thus amenable to recovery as a bottoms fraction. As the olefin is generally lower boiling than both the epoxide and the secondary alcohol, any unreacted olefin in the epoxidation reaction mixture may also be readily removed from such mixture by distillation. In certain embodiments, the excess olefin may be removed together with epoxide by flash distillation. Fractional distillation or condensation is thereafter utilized to separate the olefin from the epoxide. In other embodiments, the olefin is first removed from the epoxidation reaction mixture, followed by the epoxide. Where the olefin is propylene, for example, as much of the propylene as possible is preferably distilled overhead at a pressure of approximately 275 psig while not exceeding a bottoms temperature of about 115° C. and a hold-up time of about 10 minutes. Thereafter, the epoxide (e.g., propylene oxide) together with any remaining olefin may be distilled overhead; suitable conditions for effecting such a distillation may be, for example, a bottoms temperature of about 115° C. and a pressure of about 35 psig.

The crude alcohol stream thereby obtained is thereafter recycled at least in part for use as the diluent in the epoxidation step. An important advantage of the process of this invention is that no further purification or processing of the crude alcohol stream is necessary in order to attain satisfactory results. It may, however, be desirable to remove excessive amounts of any $C_3$-$C_4$ ketone by-product which may have formed during epoxidation; such removal may be effected, for example, by fractional distillation. If not all of the crude alcohol stream is utilized as diluent, the remainder may be recycled for use as a feed stream in the secondary alcohol oxidation step.

In the hydrogenation step, the ketone separated from the oxidant mixture is converted back to the corresponding secondary alcohol by reacting the hydrogen in the presence of a transition metal hydrogenation catalyst. Methods of converting aliphatic ketones such as acetone and 2-butanone to their corresponding secondary aliphatic alcohols by catalytic hydrogenation using a transition metal catalyst and hydrogen gas are well-known.

The transition metal in the hydrogenation catalyst is most preferably palladium, platinum, chromium (as in copper chromite, for example), rhodium, nickel, or ruthenium. If water is present, the use of Raney nickel or molybdenum-promoted nickel is especially advantageous. The hydrogenation is suitably carried out in either a liquid or vapor phase.

The temperature, hydrogen pressure, and catalyst concentration during hydrogenation are selected so as to accomplish substantial (i.e., at least 80% and more preferably at least 96%) conversion of the ketone to secondary alcohol within a practicably short reaction time (i.e., approximately 15 minutes to 12 hours) without overreduction of the ketone. The optimum hydrogenation conditions will vary depending upon the type of catalyst selected for use and the reactivity of the ketone, but may be readily determined by one skilled in the art with minimal experimentation based on the known art pertaining to ketone hydrogenation. Typically, temperatures of from about 20° C. to 175° C. and hydrogen pressures of from about 0.5 to 100 atmospheres will be appropriate for use. Preferably, the molar ratio of $H_2$ to ketone is from about 1:1 to 4:1. The amount of catalyst employed is preferably sufficient to permit weight hourly space velocities of from 0.1 to 10 grams of ketone per gram of catalyst per hour.

The hydrogenation step may be carried out in a batch, semi-batch, continuous, or semi-continuous manner using any suitable reaction vessel or apparatus wherein the ketone may be intimately contacted with the transition metal hydrogenation catalyst and hydrogen. As the catalyst is normally heterogeneous in nature, fixed bed or slurry-type reactors are especially convenient for use. A trickle bed system may also be utilized.

FIG. 1 illustrates one embodiment of the integrated epoxidation process of the invention wherein propylene is catalytically epoxidized to yield propylene oxide. A stream comprised of secondary alcohol passes via line 1 into alcohol oxidation zone 2 wherein the secondary alcohol is partially reacted with molecular oxygen to form an oxidant mixture comprised of hydrogen peroxide, ketone, and excess secondary alcohol. The molecular oxygen is provided by air or pure or diluted $O_2$ introduced via line 3.

The oxidant mixture containing hydrogen peroxide, ketone, and secondary alcohol passes from zone 2 via line 4 into oxidant distillation zone 5. In 5, the oxidant mixture is subjected to fractional distillation. Ketone is taken overhead (together, in some cases, with a portion of the secondary alcohol) and into hydrogenation zone 6 via line 7. The bottoms fraction (i.e., the concentrated hydrogen peroxide-containing stream), which contains hydrogen peroxide and secondary alcohol, is carried forward via line 8 for use in epoxidation.

The olefin to be epoxidized is fed into epoxidation zone 11 by way of lines 9 and 10. In the particular embodiment shown on FIG. 1, lines 8 and 19 also feed into line 10 at points separated from line 9. However, numerous other ways of introducing the various feed streams into epoxidation zone 11 are feasible. For example, the contents of lines 8 and 19 may be combined in a common line prior to entering line 10. Alternatively, the olefin, the crude alcohol stream, and the concentrated hydrogen peroxide-containing stream, may be separately introduced directly into epoxidation zone 11. The sequence of introducing the various reaction components to the epoxidation zone thus is not critical to the present invention, provided that the net effect is to dilute the concentrated hydrogen peroxide-containing stream with the crude alcohol stream (wherein the $H_2O_2$ concentration at all points within the liquid phase contained in the epoxidation zone is preferably less than 10 weight percent).

The titanium silicalite catalyst is preferably deployed in zone 11 as a fixed bed, although a slurry configuration could also be employed. The olefin, concentrated hydrogen peroxide-containing stream and crude alcohol stream are maintained at the desired reaction temperature in contact with the titanium silicalite within zone 11 for a time sufficient to convert at least a portion of the olefin to the corresponding ($C_3$-$C_4$ epoxide, thereby consuming most or all of the hydrogen peroxide and generating water as a co-product. The epoxidation reaction mixture thus produced passes through line 12 to olefin recovery zone 13 wherein unreacted olefin is separated by an appropriate means such as distillation and recycled to epoxidation zone 11 via lines 14 and 10. The remainder of the epoxidation reaction mixture is taken on via line 15 to epoxide purification zone 16 wherein the propylene oxide is separated by an appropriate means such as distillation and removed via line 17. Removal of the epoxide and unreacted olefin from the epoxidation reaction mixture generates a crude alcohol stream comprised of isopropanol and heavier substances such as water, acids, glycols, and the like but little, if any, propylene oxide. An intermediate or additional purification may, if so desired, be performed to reduce the level of $C_3$-$C_4$ ketone (if any) formed as a by-product from the secondary alcohol during epoxidation. The crude alcohol stream is transported from epoxide purification zone 16 via line 18. All, or a portion, of said crude alcohol stream may be introduced back into epoxidation zone 11 via line 19, with any remaining portion being carried ahead to alcohol purification zone 20 via line 21.

The process of this invention may be operated in cooperation with the epoxidizer oxygen recovery process described in U.S. application Ser. No. 08/365,397, filed Dec. 28, 1994 (Attorney's Docket No. 01-2318A) and now U.S. Pat. No. 5,468,885. The crude alcohol stream may be contacted with an olefin/oxygen purge gas withdrawn from the epoxidation zone to absorb olefin while an inert gas such as methane is added to avoid formation of flammable oxygen-containing gas compositions. The crude alcohol stream containing absorbed olefin is thereafter recycled and used as diluent in the epoxidizer.

The overhead stream from oxidant distillation zone 5 is passed via line 7 into hydrogenation zone 6 wherein the stream is reacted with hydrogen (introduced via line 22) in the presence of a suitable hydrogenation catalyst such as supported ruthenium or molybdenum—promoted Raney nickel (which is preferably deployed as a fixed bed within zone 6) so as to convert at least a portion and preferably substantially all (e.g., over 95%) of the ketone back to secondary alcohol. The hydrogenation stream withdrawn from zone 6 via line 23 may be, if so desired, further purified in alcohol purification zone 20 or, alternatively, may be passed directly back to alcohol oxidation zone 2.

Alcohol purification zone 20 is operated such that the purified secondary alcohol (or an azeotrope of the alcohol with water) is taken overhead and an aqueous stream containing at least a portion of the water generated as a co-product from the hydrogen peroxide during epoxidation as well as the heavier epoxidation by-products (acids, glycols) is generated as a bottoms fraction and removed via line 24. The purified secondary alcohol or azeotrope thereof is returned to alcohol oxidation zone 2 via lines 25 and 1. Make-up secondary alcohol may be introduced into the stream of purified secondary alcohol through line 26.

From the foregoing description, one skilled in the art can readily ascertain the essential characteristics of this invention, and, without departing from the spirit and scope thereof, can make various changes and modifications of the invention to adapt it to various usages, conditions, and embodiments.

EXAMPLES

A hydrogen peroxide-containing feed for propylene epoxidation was prepared by combining 820 g isopropanol, 120 g water, 60 g $H_2O_2$ (50% in water), 5.0 g aqueous ammonium acetate (1 wt % solution), 2.0 g acetic acid, and 0.26 g formic acid. Epoxidation was performed using propylene (5 equivalents) at 60° C. and 250 psig over 2.0 g TS-1 titanium silicalite catalyst packed in a ⅜" stainless steel tube containing 60 cc quartz chips. The hydrogen peroxide-containing feed was introduced at a rate of 70 mL/hour. Analysis of the product by gas chromatography and iodiometric titration indicated 99% hydrogen peroxide conversion, 89% selectivity to propylene oxide, 6% selectivity to ring-opened products (glycols, glycol ethers), and 5% selectivity to oxygen. The propylene oxide and excess propylene were removed by distillation. The distillation bottoms, which contained 80% isopropanol, 18% water, 2% ring-opened products and 15 ppm $NH^+_4$, were used as the recycle feed (crude alcohol stream) in the following examples.

An additional feed was prepared to resemble isopropanol oxidant mixture after removal of the acetone by distillation by combining 46 g isopropanol, 27 g $H_2O_2$ (50% aqueous solution), 0.37 g acetic acid, and 0.13 g formic acid. The feed which contained 18.45% $H_2O_2$ by iodometric titration, was used as the fresh oxidant in the following examples.

EXAMPLE 1

A Parr reactor equipped with an internal thermowell and dip tube attached to a propylene cylinder was charged with 24.0 g of the above-described recycle feed, 9.0 g of the above-identified fresh oxidant (0.0488 mol $H_2O_2$), 0.45 TS-1 titanium silicalite catalyst, and 0.384 g 1% aqueous ammonium acetate solution ($5.0 \times 10^{-5}$ mol; 34 ppm $NH^+_4$). The reactor was flushed with helium and then charged with 16 mL propylene (0.20 mol.) The reactor was submerged in an oil bath and the reaction mixture stirred at 56° C. for one hour. The reactor was chilled to 18° C. and then vented into a gas bag. The bag was analyzed for oxygen and organic products. The remaining solution was analyzed by gas chromatography and iodometric titration. Hydrogen peroxide conversion was 98%. Selectivities were 88% to propylene oxide, 6% to acetone, 3% to oxygen, and 3% to ring-opened products (after correction for the initial level of ring-opened products in the recycle feed). Despite the use of the crude recycle feed as a diluent, selectivity to the desired epoxide product was essentially identical to that observed using fresh oxidant (see Comparative Examples 5 and 6 below).

EXAMPLE 2

Example 1 was repeated using 0.121 g 1% aqueous ammonium acetate solution ($1.6 \times 10^{-5}$ mol; 11 ppm $NH^+_4$) and 14 mL (0.17 mol) propylene. Hydrogen peroxide conversion was 98%. Selectivities were 86% to propylene oxide, 5% to acetone, 2% to oxygen, and 7% to ring-opened products.

EXAMPLE 3

Example 2 was repeated using 0.413 g 1% aqueous sodium acetate solution ($5.0 \times 10^{-5}$ mol; 47 ppm $Na^+$) instead of ammonium acetate. Hydrogen peroxide conversion was 97%. Selectivites were 87% to propylene oxide, 5% to acetone, 3% to oxygen, and 5% to ring-opened products.

EXAMPLE 4

Example 2 was repeated using 0.816 g 1% aqueous lithium nitrate solution ($1.2 \times 10^{-4}$ mol; 27 ppm $Li^+$) instead of ammonium acetate. Hydrogen peroxide conversion was 94%. Selectivities were 84% to propylene oxide, 4% to acetone, 2% to oxygen, and 10% to ring-opened products.

COMPARATIVE EXAMPLE 5

This example demonstrates that the process of the invention, which utilizes a stream recycled from epoxidation as a diluent, provides epoxide selectivities comparable to those obtained using fresh isopropanol oxidant. Fresh oxidant mixture was prepared by combining 67 g isopropanol, 10 g $H_2O_2$, 23 g water, 0.20 g acetic acid, and 0.025 g formic acid. The oxidant mixture contained 5.11% $H_2O_2$ by iodiometric titration. A Parr reactor equipped with an internal thermowell and dip tube attached to a propylene cylinder was charged with 33.0 g fresh oxidant mixture (0.050 mol $H_2O_2$), 0.45 g TS-1 titanium silicalite, and 0.435 g 1% aqueous ammonium acetate solution ($5.6 \times 10^{-5}$ mol; 39 ppm $NH^+_4$). The reactor was flushed with helium and charged with 20 mL propylene (0.25 mol). The reactor was submerged in an oil bath and stirred at 53° C. for one hour. The reactor was chilled to 18° C. and vented into a gas bag. Conversion of hydrogen peroxide was 95%. Selectivities were 89% to propylene oxide, 5% to acetone, 2% to oxygen, and 3% to ring-opened products.

COMPARATIVE EXAMPLE 6

Comparative Example 5 was repeated using 0.298 g 1% aqueous ammonium acetate solution ($3.9 \times 10^{-5}$ mol; 27 ppm $NH^+_4$). Hydrogen peroxide conversion was 94%. Selectivities were 87% to propylene oxide, 6% to acetone, 1% to oxygen, and 6% to ring-opened products.

We claim:

1. An integrated epoxidation process comprising
   (a) reacting a $C_3$-$C_4$ secondary alcohol and molecular oxygen in a liquid phase to form an oxidant mixture comprised of the $C_3$-$C_4$ secondary alcohol, a $C_3$-$C_4$ aliphatic ketone corresponding to the $C_3$-$C_4$ secondary alcohol, and hydrogen peroxide;
   (b) separating substantially all of the $C_3$-$C_4$ ketone from the oxidant mixture to provide a concentrated hydrogen peroxide-containing stream comprised of $C_3$-$C_4$ secondary alcohol, hydrogen peroxide, and less than 1 weight percent $C_3$-$C_4$ ketone;
   (c) reacting the concentrated hydrogen peroxide-containing stream with a $C_2$-$C_4$ olefin in the presence of a titanium silicalite catalyst and a diluent to form an epoxidation reaction mixture comprised of a $C_2$-$C_4$ epoxide corresponding to the $C_2$-$C_4$ olefin, water, and $C_3$-$C_4$ secondary alcohol;
   (d) separating substantially all of the $C_2$-$C_4$ epoxide from the epoxidation reaction mixture to form a crude alcohol stream comprised of water, the $C_3$-$C_4$ secondary alcohol, and less than 1 weight percent of the $C_2$-$C_4$ epoxide; and (e) recycling at least a portion of the crude alcohol stream for use as at least a portion of the diluent in step (c).

2. The integrated epoxidation process of claim 1 wherein the $C_3$-$C_4$ ketone separated from the oxidant mixture in step (b) is hydrogenated to the $C_3$-$C_4$ secondary alcohol.

3. The integrated epoxidation process of claim 1 wherein the $C_2$-$C_4$ olefin is propylene.

4. The integrated epoxidation process of claim 1 wherein the ($C_3$-$C_4$ secondary alcohol is isopropanol.

5. The integrated epoxidation process of claim 1 wherein the concentrated hydrogen peroxide-containing stream is comprised of from 5 to 30 weight percent hydrogen peroxide.

6. The integrated epoxidation process of claim 1 wherein the diluent is present in an amount sufficient to provide a hydrogen peroxide concentration of less than 10 weight percent based on the total weight of concentrated hydrogen peroxide-containing stream and diluent in step (c).

7. The integrated epoxidation process of claim 1 wherein the titanium silicalite has an MFI, MEL, or zeolite beta topology.

8. The integrated epoxidation process of claim 1 wherein the titanium silicalite has a composition corresponding to the chemical formula $xTiO_2$:$(1-x)$ $SiO_2$ wherein x is from 0.01 to 0.125.

9. The integrated epoxidation process of claim 1 wherein separation step (b) is accomplished by distillation whereby substantially all of the $C_3$-$C_4$ ketone is vaporized and removed from the oxidant mixture as an overhead stream.

10. The integrated epoxidation process of claim 1 wherein step (a) is performed at a temperature of from 50° C. to 200° C.

11. The integrated epoxidation process of claim 1 wherein step (c) is performed at a temperature of from 25° C. to 120° C.

12. An integrated epoxidation process comprising (a) reacting isopropanol and molecular oxygen in a liquid phase at a temperature of from 50° C. to 200° C. to form an oxidant mixture comprised of isopropanol, acetone, and hydrogen peroxide;

(b) subjecting the oxidant mixture to distillation whereby substantially all of the acetone is vaporized and removed from the oxidant mixture as an overhead stream so as to provide a concentrated hydrogen peroxide-containing stream comprised of isopropanol, from 10 to 30 weight percent hydrogen peroxide, and less than 1 weight percent acetone;

(c) reacting the concentrated hydrogen peroxide-containing stream with propylene at a temperature of from 25° C. to 120° C. in the presence of a titanium silicalite catalyst and a diluent to form an epoxidation reaction mixture comprised of water, propylene oxide and isopropanol;

(d) separating substantially all of the propylene oxide from the epoxidation reaction mixture by distillation to form a bottoms stream comprised of water, isopropanol and less than 1 weight percent of propylene oxide;

(e) recycling at least a portion of the bottoms stream for use as at least a portion of the diluent in step (c);

(f) hydrogenating the acetone separated from the oxidant mixture in step (b) to isopropanol; and (g) recycling at least a portion of the isopropanol from step (f) for use in step (a).

13. The integrated epoxidation process of claim 12 wherein step (f) is performed in the presence of a hydrogenation catalyst comprised of a transition metal selected from palladium, platinum, ruthenium, chromium, rhodium, and nickel at a temperature of 20° to 175° C. and a hydrogen pressure of 0.5 to 100 atmospheres.

14. The integrated epoxidation process of claim 12 wherein the titanium silicalite is deployed in the form of a fixed bed.

15. The integrated epoxidation process of claim 12 wherein the molar ratio of propylene: hydrogen peroxide in step (c) is from 1:2 to 10:1.

16. The integrated epoxidation process of claim 12 wherein step (a) is performed at a partial oxygen pressure of from 5 to 50 psia.

17. The integrated epoxidation process of claim 12 wherein the diluent is present in an amount sufficient to provide a hydrogen peroxide concentration in step (c) of at least 1 but less than 10 weight percent based on the total weight of concentrated hydrogen peroxide-containing stream and diluent.

18. The integrated epoxidation process of claim 12 wherein an excess of propylene relative to hydrogen peroxide is present in step (c) and the excess propylene is separated from the epoxidation reaction mixture after step (c) and before step (e).

19. The integrated epoxidation process of claim 12 wherein the titanium silicalite catalyst is used in combination with a support.

* * * * *